United States Patent [19]
Chwalisz et al.

[11] Patent Number: 4,891,368
[45] Date of Patent: Jan. 2, 1990

[54] USE OF ANTIGESTAGENS FOR SOFTENING THE NONPREGNANT CERVIX

[75] Inventors: Krzysztof Chwalisz; Sybille Beier; Angelika Esch; Walter Elger, all of Berlin, Fed. Rep. of Germany

[73] Assignee: Schering Aktiengesellschaft, Berlin and Bergkamen, Fed. Rep. of Germany

[21] Appl. No.: 287,258

[22] Filed: Dec. 21, 1988

[30] Foreign Application Priority Data

Dec. 21, 1987 [DE] Fed. Rep. of Germany ....... 3744054

[51] Int. Cl.$^4$ .................... A61K 31/56; A61K 31/135

[52] U.S. Cl. ...................................... 514/179; 514/647
[58] Field of Search ................... 514/179, 647

[56]       References Cited
        U.S. PATENT DOCUMENTS 4,424,159  1/1984  Biollaz ............................. 260/397.4
4,780,461 10/1988  Neef et al. ......................... 514/179

Primary Examiner—Douglas W. Robinson
Assistant Examiner—Joseph A. Lipovsky
Attorney, Agent, or Firm—Millen, White & Zelano

[57]            ABSTRACT

Antigestagens are useful for softening the nonpregnant cervix.

10 Claims, 4 Drawing Sheets

USE OF ANTIGESTAGENS FOR SOFTENING THE NONPREGNANT CERVIX

SUMMARY OF THE INVENTION

The invention relates to the use, not during pregnancy, of antigestagens for the production of pharmaceutical agents with a cervix-softening effect.

It is known that antigestagens, such as, for example, 11beta-[(4-N,N-dimethylamino)-phenyl]-17alpha-hydroxy-17beta-(3-hydroxypropyl)-13alpha-methyl-4,9(10)-gonadien-3-one influence the cervix during pregnancy. In animals that are not pregnant and that are at the beginning of pregnancy, the cervix is very firm. In the second half of pregnancy, a progressive softening and dilation of the cervix occurs and it reaches a maximum shortly before birth. Cervix softening and dilation can be induced with antigestagens during pregnancy [Acta Endocrinol. (Copenhagen) Suppl. 283 (1987) 113].

It has now been found that the cervix-softening effect of antigestagens is not limited to the pregnant cervix.

BRIEF DESCRIPTION OF THE DRAWINGS

Various other objects, features and attendant advantages of the present invention will be more fully appreciated as the same becomes better understood when considered in conjunction with the accompanying drawings wherein.

DETAILED DESCRIPTION

Figure 1A:
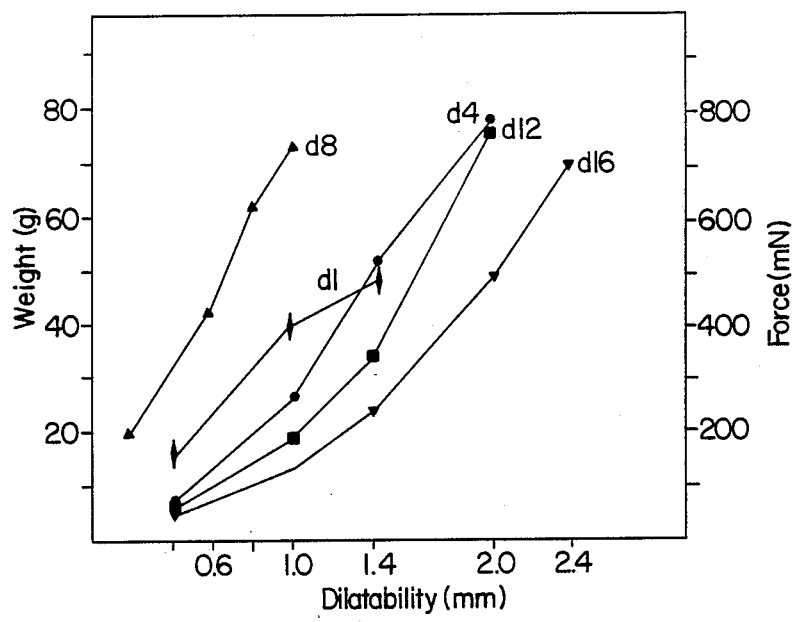
FIG. 1(a) shows the dilatability of the cervix in untreated cyclic guinea pigs.
Figure 1B:
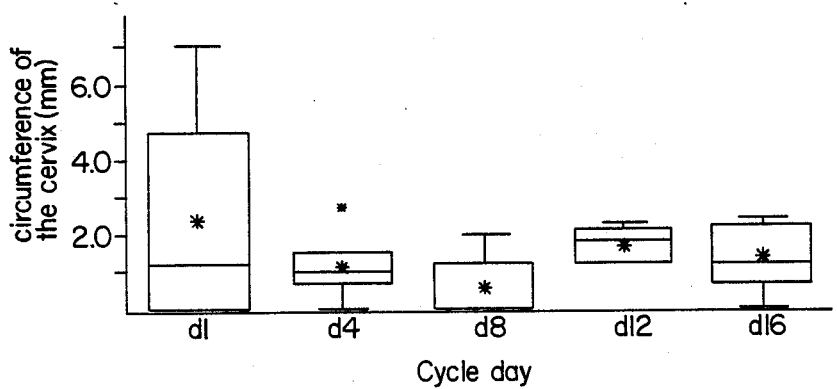
FIG. 1(b) shows the same cyclic variation in the spontaneous inner circumference of the cervix of the untreated cyclic guinea pig.
Figure 2:
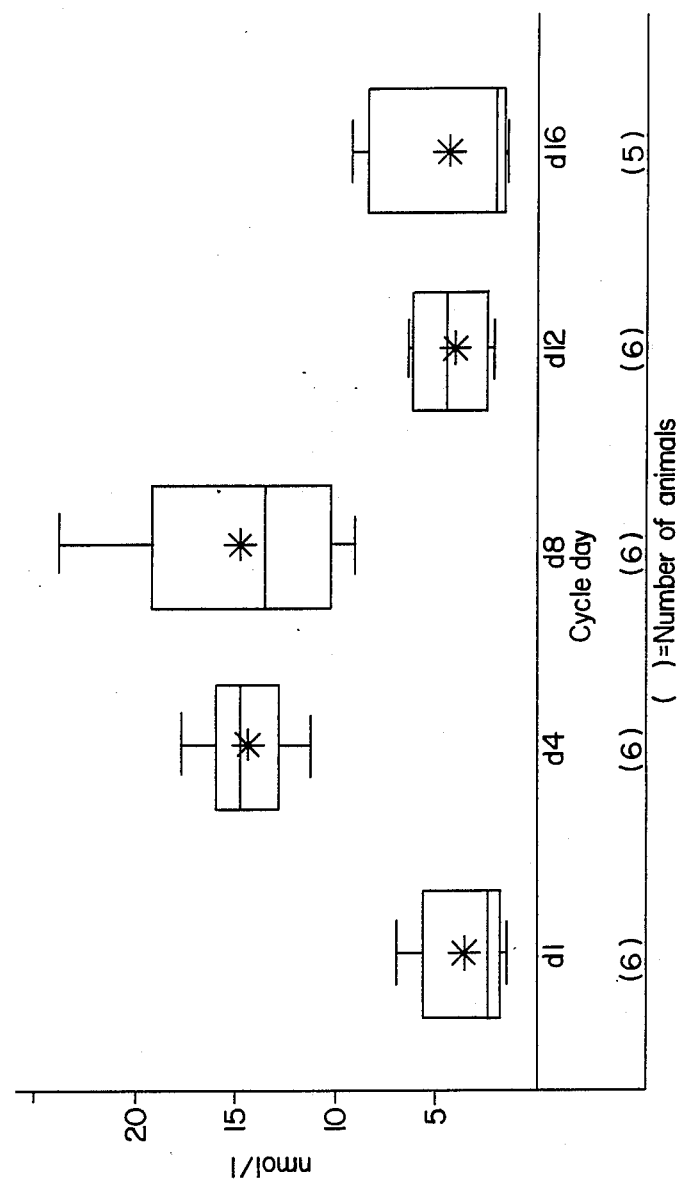
FIG. 2 shows the cyclic variation in the plasma progesterone concentrations in the untreated cyclic guinea pig, which varies inversely with the dilatability of the cervix and inner circumference of the cervix (FIG. 1)

In nonpregnant animals, the cyclical changes of the dilatability of the cervix are in an inverse relationship to the serum progesterone level (see FIGS. 1 and 2). In guinea pigs, on the 8th cycle day, when the progesterone levels are the highest, a very firm cervix is found. After administration of antigestagens, softening of the cervix is surprisingly observed, despite the increase in serum progesterone levels during the treatment period (see FIGS. 3 and 4).

The antigestagen treatment according to the invention can also be used in human medicine in nonpregnant women, in particular as a pretreatment before various medical procedures on the uterus which require insertion of objects through the cervix, such as, for example, hysteroscopy, insertion of an IUD or curettage. Pain and injuries to the cervix are avoided to a large extent by the treatment according to the invention.

Depending on the desired effect, the treatment can be performed once or several times; generally, the treatment is performed once daily for 1 to 4 days before the medical procedure.

According to this invention, the antigestagens can be used in amounts of generally 2 to 50 mg, preferably 5 to 20 mg of 11beta-[(4-N,N-dimethylamino)-phenyl]-17alpha-hydroxy-17beta-(3-hydroxypropyl)-13alpha-methyl-4,9(10)-gonadien-3-one per day, or a biologically equivalent amount of another antigestagen. These biologically equivalent amounts can be determined routinely and conventionally, e.g., by performing differential potency studies using fully routine pharmacological protocols, e.g., as disclosed in Acta Endocrinologica, Suppl. 283, Copenhagen 1987, p. 113/114 (there measured in vitro on the isolated uterine cervix of pregnant guinea pigs).

Suitable antigestagens include all compounds which have a strong affinity for the gestagen receptor (progesterone receptor) and, moreover, have no intrinsic gestagen activity. Nonlimiting examples of suitable competitive progesterone antagonists include the following steroids:

11beta-[(4-N,N-dimethylamino)-phenyl]-17beta-hydroxy-17alpha-propynyl-4,9(10)-estradien-3-one, 11beta-[(4-N,N-dimethylamino)-phenyl]-17beta-hydroxy-18-methyl-17-alpha-propynyl-4,9(10)-estradien-3-one and 11beta-[(4-N,N-dimethylamino-phenyl]-17abeta-hydroxy-17aalpha-propynyl-D-homo-4,9(10)-16-estratrien-3-one (European patent application 82400025.1. Publication number 0 057 115); and furthermore 11beta-methoxyphenyl-17beta-hydroxy-17alpha-ethynyl-4,9(10)-estradien-3-one (Steroids 37 (1981) 361–382), 11beta-[(4-N,N-dimethylamino)-phenyl]-17beta-hydroxy-17alpha-(hydroxyprop-1-(Z)-enyl)-4,9(10)-estradien-3-one (European patent application 847300147.0. Publication number 0 147 361), and 11beta-[(4-N,N-dimethylamino)-phenyl]-17alpha-hydroxy-17beta-(3-hyroxypropyl)-13alpha-methyl-4,9(10)-gonadien-3-one (European patent application 84730062.1. Publication number 0 129 499).

The foregoing listing is exemplary only. Many other antigestagens can be used, e.g., as disclosed in Fertility and Sterility 40, 253 (1983), Steroids 37, 361–382 (1981). EP 0 057 115 and EP 0 283 428.

The antigestagens can be applied, for example, locally, topically, enterally or parenterally.

For the preferred oral application, tablets, coated tablets, capsules, pills, suspensions or solutions are especially suitable that can be produced in the usual way with the admixtures and vehicles usual in galenic medicine. For local or topical use, vaginal suppositories, vaginal gel or transdermal systems such as skin plasters are suitable.

For topical use preferably a gel volume of from 1 ml to 2,5 ml is applied (dosage range of the active ingredient per application is from 0,5 mg to 25,0 mg).

One dosage unit contains about 2 to 50 mg of 11beta-[(4-N,N-dimethylamino)-phenyl]-17-alpha-hydroxy-17beta-(3-hydroxypropyl)-13alpha-methyl-4,9(10)-gonadien-3-one or a biologically equivalent amount of another antigestagen.

EXAMPLES

Example 1

Composition of a tablet with 10 mg of 11beta-[(4,N,N-dimethylamino)-phenyl]-17alpha-hydroxy-17beta-(3-hydroxypropyl)-13alpha-methyl-4,9(10)-gonadien-3-one for oral application.

10.0 mg of 11beta-[(4-N,N-dimethylamino)-phenyl]-17alpha-hydroxy-17beta-(3-hydroxypropyl)-13alpha-methyl-4,9(10)-gonadien-3-one

| | |
|---|---|
| 140.5 mg | of lactose |
| 69.5 mg | of cornstarch |
| 2.5 mg | of polyvinylpyrrolidone 25 |
| 2.0 g | of Aerosil |
| 0.5 mg | of magnesium stearate |
| 225.0 mg | total weight |

Example 2

Composition of an oily solution with 50 mg of 11beta-[(4-N,N-dimethylamino)-phenyl]-17alpha-hydroxy-17beta-(3-hydroxypropyl)-13alpha-methyl-4,9(10)-gonadien-3-one for parenteral application.

50 mg of the antigestagen is dissolved in 1 ml each of castor oil/benzyl benzoate in a volume ratio of 6:4.

Example 3

Composition and manufacture of lipophilic gels containing
 (a) 0.05% b.w. of antigestagen
 (b) 1,0% b.w. of antigestagen

| | | |
|---|---|---|
| 0.5 mg | 10.0 mg | 11β-[(4-N,N—Dimethyl-amino)-phenyl]-17α-hydroxy-17β-(3-hydroxy-propyl)-13α-methyl-4,9(10)-gonadien-3-on |
| 47.0 mg | 47.0 mg | Benzylbenzoate |
| 887.5 mg | 878.0 mg | Neutralol (Miglyol 812 ®) |
| 65.0 mg | 65.0 mg | colloid silicon dioxide (Aerosil 200 ®) |
| 1,000.0 mg | 1,000.0 mg | lipophilic gel |

For the manufacture firstly the liquid components are added in portions to the antigestagen under stirring which is continued until a homogeneous suspension or solution is obtained. Into the suspension or solution the silicon dioxide is incorporated as a builder for the gel. After having allowed to rest for about 24 hours the gel is portioned, e.g. in syringes or tubes made of plastics.

Example 4

Composition and manufacture of hydrophilic gel containing
 (a) 0.05% b.w. of antigestagen
 (b) 1,0% b.w. of antigestagen

| | | |
|---|---|---|
| 0.5 mg | 10.0 mg | antigestagen (v.s.)* |
| 180.0 mg | 180.0 mg | poloxamer (Pluronic F 127 ®) |
| 819.5 mg | 810.0 mg | bidestillated water |
| 1,000.0 mg | 1,000.0 mg | hydrophilic gel |

*as in Example 3

For the production of the hydrophilic gel the antigestagen is suspended in the poloxamer which was dissolved in cold water; suspending can take place directly before the application. The raised temperature at the place of action will lead to a hardening of the gel.

The lypophilic as well as the hydrophilic gels of the Examples 3a, b) and 4a, b), respectively can be manufactured in a sterile manner by way of the usual procedures for the reduction of the number of germs.

Pharmacological observations

Treated groups

Nonpregnant guinea pigs received daily, from the 8th to the 11th day of the approximately 16-day cycle (luteal phase), 10 mg of 11beta-[(4-N,N-dimethylamino)-phenyl]-17alpha-hydroxy-17beta-(3-hydroxypropyl)-13alpha-methyl-4,9(10)-gonadien-3-one (A) or 10 mg of 11beta-[(4-N,N-dimethylamino)-phenyl]-17beta-hydroxy-17alpha-propynyl-4,9(10)-estradien-3-one (B).

The test substances were dissolved in 1 ml of benzyl benzoate/castor oil (1:2) and injected subcutaneously.

Control groups

One group of guinea pigs was treated from the 8th to the 11th day of the cycle with the vehicle.

In the second group of the animals the hysterectomy occured on the 8th cycle day.

Performance of measurements

The dilatability of the cervix was measured in vitro on 12th cycle day with a specially constructed device (DE-P-37 19 380, DE-P-37 19 381). On the same day the serum progesterone values were determined.

Result

Figure 3:
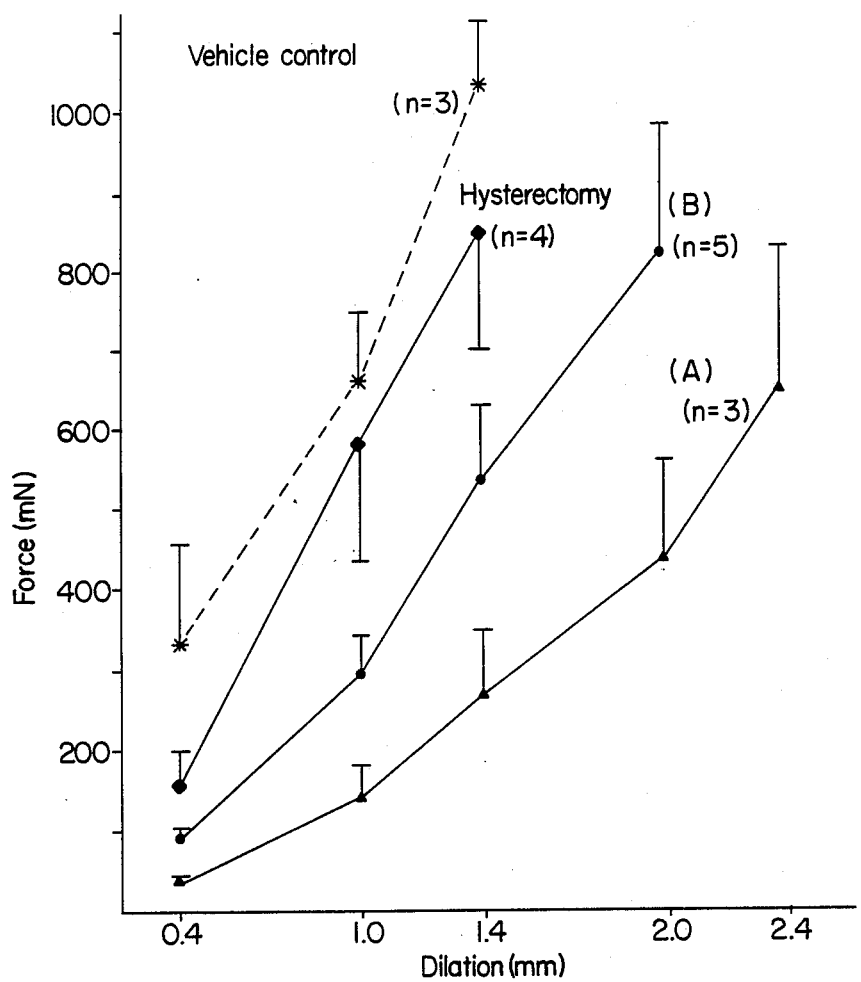
FIG. 3 shows the dilatability of the cervix in control cyclic guinea pigs, after treatment with antigestagens A (11beta-[(4-N,N-dimethylamino)-phenyl]-17alpha-hydroxy-17beta-(3-hydroxypropyl)-13alpha-methyl-4,9(10)-gonadien-3-one) and B (11beta-[(4-N,N-dimethylamino)-phenyl]-17-beta-hydroxy-17-alpha-propynyl-4,9(10)-estradien-3-one), and after hysterectomy. Hysterectomized guinea pigs are used as a control to show that the antigestagens act directly on the cervix.
Figure 4:
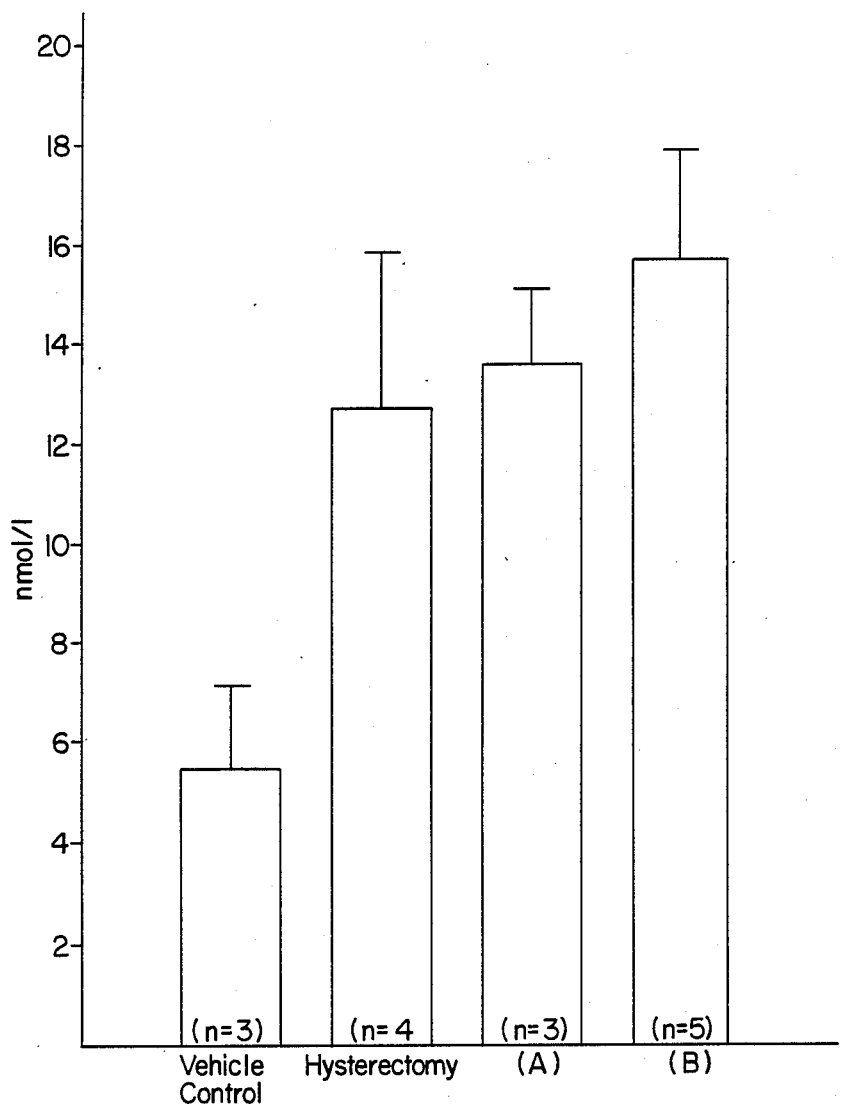
FIG. 4 shows the serum progesterone concentrations in control cyclic guinea pigs, after treatment with antigestagens, and after hysterectomy.

It can be seen from FIGS. 3 and 4 that on the 12th cycle day the dilatability of the cervix in the animals treated with antigestagens rise sharply compared with the controls. The serum progesterone values in both treated groups A and B were raised compared with the vehicel controls and correspond to those of the second control group (i.e. after hysterectomy). Hysterectomy as well as treatment with antigestagens lead to an antiluteolytic effect, i.e. to high progesterone values on 12th day of the cycle.

This finding shows that the antigestagen directly acts on the cervix as though hysterectomy causes serum progesterone levels comparable to those caused by the antigestagens the cervix remains rigid after hysterectomy.

The preceding examples can be repreated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of preparing a nonpregnant mammalian female for a uterine medical procedure comprising administering to said individual prior to said procedure an antigestagen in an amount effective to soften the cervix.

2. A method of claim 1, wherein the antigestagen is 11beta-[(4,N,N-dimethylamino)-phenyl]-17beta-hydroxy-17alpha-propynyl-4,9(10)-estradien-3-one, 11beta-[(4-N,N-dimethylamino)-phenyl]-17beta-hydroxy-18-methyl-17alpha-propynyl-4,9(10)-estradien-3-one, 11beta-[(4-N,N-dimethylamino)-phenyl]-17abeta-hydroxy-17aalpha-propynyl-D-homo-4,9(10)-16-estratrien-3-one, 11beta-methoxyphenyl-17beta-hydroxy-17alpha-ethynyl-4,9(10)-estradien-3-one, 11beta-[(4-N,N-dimethylamino)-phenyl]-17beta-hydroxy-17alpha-(hydroxyprop-1-(Z)-enyl)-4,9(10)-estradien-3-one, or 11beta-[(4-N,N-dimethylamino)-phenyl]-17alpha-hydroxy-17beta-(3-hydroxypropyl)-13alpha-methyl-4,9(10)-gonadien-3-one.

3. A method of claim 2, wherein the antigestagen is 11beta-[(4-N,N-dimethylamino)-phenyl]-17alpha-hydroxy-17beta-(3-hydroxypropyl)-13alpha-methyl-4,9(10)-gonadien-3-one.

4. A method of claim 2, wherein the amount of said antigestagen administered is 2-50 mg per day.

5. A method of claim 2, wherein the amount of said antigestagen administered is 5-20 mg per day.

6. A method of claim 1, wherein the amount of said antigestagen administered is 2-50 mg per day.

7. A method of claim 1, wherein the amount of said antigestagen administered is 5-20 mg per day.

8. A method of claim 1, wherein said procedure is a hysteroscopy.

9. A method of claim 1, wherein said procedure is insertion of an IUD.

10. A method of claim 1, wherein said procedure is a curettage.

* * * * *